US012714674B2

(12) United States Patent
Stirm

(10) Patent No.: US 12,714,674 B2
(45) Date of Patent: Aug. 25, 2026

(54) JAK INHIBITORS HAVING A SPECIFIC PARTICLE SIZE DISTRIBUTION

(71) Applicant: Elanco US Inc., Indianapolis, IN (US)

(72) Inventor: Stephen Stirm, Indianapolis, IN (US)

(73) Assignee: Elanco US Inc., Indianapolis, IN (US)

( * ) Notice: Subject to any disclaimer, the term of this patent is extended or adjusted under 35 U.S.C. 154(b) by 296 days.

(21) Appl. No.: 18/249,869

(22) PCT Filed: Oct. 25, 2021

(86) PCT No.: PCT/US2021/056403

§ 371 (c)(1),
(2) Date: Apr. 20, 2023

(87) PCT Pub. No.: WO2022/087515

PCT Pub. Date: Apr. 28, 2022

(65) Prior Publication Data

US 2023/0404925 A1 Dec. 21, 2023

Related U.S. Application Data

(60) Provisional application No. 63/105,147, filed on Oct. 23, 2020.

(51) Int. Cl.

| | |
|---|---|
| ***A61K 9/28*** | (2006.01) |
| ***A61K 9/14*** | (2006.01) |
| ***A61K 31/519*** | (2006.01) |
| ***A61K 47/02*** | (2006.01) |
| ***A61K 47/38*** | (2006.01) |
| ***A61P 17/04*** | (2006.01) |

(52) U.S. Cl.

CPC .................. *A61K 9/28* (2013.01); *A61K 9/14* (2013.01); *A61K 31/519* (2013.01); *A61K 47/02* (2013.01); *A61K 47/38* (2013.01); *A61P 17/04* (2018.01)

(58) Field of Classification Search

CPC ...... A61K 31/519; A61K 47/02; A61K 47/38; A61K 9/0053; A61K 9/14; A61K 9/167; A61K 9/2009; A61K 9/2054; A61K 9/2059; A61K 9/28; A61K 9/2077; A61P 17/00; A61P 17/04; C07D 487/04

See application file for complete search history.

(56) References Cited

U.S. PATENT DOCUMENTS

| | | | |
|---|---|---|---|
| 2018/0044342 | A1 | 2/2018 | Chen et al. |
| 2020/0339585 | A1 | 10/2020 | Hu |
| 2023/0404925 | A1 | 12/2023 | Stirm |

FOREIGN PATENT DOCUMENTS

| | | | | |
|---|---|---|---|---|
| CL | 2009000576 | A1 | 6/2009 | |
| CN | 102026999 | B | 4/2011 | |
| JP | 2011514909 | A | 5/2011 | |
| RU | 2619944 | C2 | 5/2017 | |
| WO | 2002000196 | A2 | 1/2002 | |
| WO | 2007070514 | A1 | 6/2007 | |
| WO | 2007070589 | A2 | 6/2007 | |
| WO | 2009114512 | A1 | 9/2009 | |
| WO | 2013173506 | A2 | 11/2013 | |
| WO | 2014128588 | A1 | 8/2014 | |
| WO | 2015044394 | A1 | 4/2015 | |
| WO | 2016141891 | A1 | 9/2016 | |
| WO | 2016205487 | A1 | 12/2016 | |
| WO | 2019003249 | A1 | 1/2019 | |
| WO | 2019121849 | A1 | 6/2019 | |
| WO | WO-2020173364 | A1 * | 9/2020 | ........... A61K 31/519 |
| WO | 2020219524 | A1 | 10/2020 | |
| WO | 2022087515 | A1 | 4/2022 | |

OTHER PUBLICATIONS

Machine Translation for WO 2020/173364; filed Feb. 20, 2020; published Sep. 3, 2020.*

Williams et al., "Content Uniformity and Dose Uniformity: Current Approaches, Statistical Analyses, and Presentation of an Alternative Approach, with Special Reference to Oral Inhalation and Nasal Drug Products", Pharmaceutical Research (2002), Apr. 19, 2002, pp. 359-366 (abstract).

<905> Uniformity of Dosage Units, Stage 6 Harmonization, The United States Pharmacopeial Convention (2011), Dec. 1, 2011, 3 pages.

K.R. Vandana et al., "An overview on in situ micronization technique—An emerging novel concept in advanced drug delivery", Saudi Pharmaceutical Journal, 2014, vol. 22, issue 4, p. 283-289.

Sherry L. Morissette et al., "High-through put crystallization: polymorphs, salts, co-crystals and solvates of pharmaceutical solids", Advanced Drug Delivery Reviews, 2004, v. 56, p. 275-300 (section 1; 3.1).

"Biopharmacy: a textbook on pharmaceutical technology" [in Russian]; compiled by G. V. Ayupova et al., Ufa: State Educational Institution of Higher Professional Education "Bashkir State Medical University" of the Russian Health Ministry, 2011, section 4.2.

I. M. Pertsev, "Pharmaceutical and Medical-Biological Aspects of Drugs" [in Russian], v. 1, 1999, p. 253-254, Kharkov, UkrFA Publishing House.

Toutain PLet [sic] al., "Species differences in pharmacokinetics and pharmacodynamics", Handbook Exp Pharmacol. 2010; (199): 19-48.

"General Pharmacopoeial Article. 1.4.2.0008.15" [in Russian], State Pharmacopoeia of the Russian Federation XIII ed., Moscow, 2015, v. 2, p. 205-207.

Ruiz F et al., "Standardized method to assess medicines' acceptability: focus on paediatric population", J Pharm Pharmacol., Apr. 2017; 69(4):406-416.

Sejal R. Ranmal, "Methodologies for assessing the acceptability of oral formulations among children and older adults: a systematic review", Drug Discovery Today, vol. 23, issue 4, 2018, p. 830-847.

Greene TW, et al., "Protective Groups in Organic Synthesis", Wiley & Sons, Inc., Apr. 9, 1999.

(Continued)

*Primary Examiner* — Jeffrey T. Palenik

(74) *Attorney, Agent, or Firm* — McBee Moore & Vanik IP, LLC

(57) ABSTRACT

The present disclosure provides compositions of 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific acceptance value and/or particle size distribution, pharmaceutical compositions comprising the same, methods of using the same, and processes for making the same.

16 Claims, No Drawings

(56) References Cited

OTHER PUBLICATIONS

The United States Pharmacopoeia, National Formulary, pp. 1843-1844, 2000.
Berge SM, et al., "Pharmaceutical salts", Journal of Pharmaceutical Sciences, vol. 66, No. 1, pp. 2-19, 1977.
Williams et al., "Content Uniformity and Dose Uniformity: Current Approaches, Statistical Analyses, and Presentation of an Alternative Approach, with Special Reference to Oral Inhalation and Nasal Drug Products," Pharmaceutical Research, Apr. 1, 2002, pp. 359-366.
"Uniformity of Dosage Units 1," USP—Stage 6 Harmonization, Dec. 1, 2011, XP05588725, pp. 1-3. Retrieved from the Internet on Jan. 17, 2025.
Sarma B. et al. Solid formation of pharmaceuticals: Polymorphs, salt and cocrystals. Korean J.Chem.Eng., 2011, 28 (2), p. 315-322.
Byrn et al., "Pharmaceutical Solids: A Strategic Approach to Regulatory Considerations", Pharmaceutical Research, 1995, vol. 12, No. 7, pp. 945-954.
Mitsuhisa Yamano, "Approach to crystal polymorphism in pharmaceutical process research", Journal of the Society of Organic Synthetic Chemistry, Sep. 1, 2007, vol. 65, No. 9, pp. 907-913.
Noriyuki Takada, "API Form Screening and Selection in Drug Discovery Stage", Pharm Stage, Jan. 15, 2007, vol. 6, No. 10, pp. 20-25.
Hiroshi Oshima, "Crystallization of Polymorphs and Pseudo-polymorphs and Its Control", Pharm Stage, Jan. 15, 2007, vol. 6, No. 10, pp. 48-53.
Yoko Kawaguchi et al., "Pharmaceuticals and crystal polymorphisms", Biotechnology Research, 2002, vol. 4, No. 2, pp. 310-317.
Office Action issued in corresponding Korean Application No. 10-2021-7033869 (Jan. 9, 2024).
Christian Reichard. Solvents and Media Effects in Organic Chemistry. Publishing House Mir, 1991, 763 p (pp. 611-614, section AS).
Caira MR, Topics in Current Chemistry (1998) 198 pp. 163-208.
Rodriguez-Spong et al. Advanced Drug Delivery Reviews (2004) 56: 241-274.
Lv Yang et al. People's Health Publishing House "Polymorphic Drugs" (2009).
Hillier A, et al., "The ACVD task force on canine atopic dermatitis (I): incidence and prevalence," Vet Immunol Immunopathol; 81:147-151 (2001).
Renauld JC, "Class II cytokine receptors and their ligands: Key antiviral and inflammatory modulators," Nat Rev Immunol. 3: 667-76 (2003).
Rybníček J et.al., "Further validation of a pruritus severity scale for use in dogs," Veterinary Dermatology, 20(2): 115-122 (2009).
Gonzales AJ et.al., "Interleukin-31: its role in canine pruritus and naturally occurring canine atopic dermatitis," Vet Dermatol 24(1): 48-53 e11-2 (2013).
Cosgrove, S. B. et al., "Efficacy and safety of oclacitinib for the control of pruritus and associated skin lesions in dogs with canine allergic dermatitis," Vet Dermatol 5(4):479-e114 (2013).
Thierry Olivry, et.al., "Validation of the Canine Atopic Dermatitis Extent and Severity Index (CADESI)-4, a simplified severity scale for assessing skin lesions of atopic dermatitis in dogs," Vet Dermatol 25: 77-e25 (2014).
Ashizawa, K. et al., "Polymorphism of Pharmaceuticals and Science of Crystallization", Japan, Maruzen Planet Co., Ltd., Sep. 20, 2002, pp. 3-16.
"Experimental Chemistry Course (Continued) 2 Separation and Purification", Maruzen Co., Ltd., Jan. 25, 1967, pp. 159-162, 184-193.
"Handbook of Chemistry: Applied Chemistry", The Chemical Society of Japan, Maruzen Co., Ltd., 6th Edition, p. 178.
"Experimental Chemistry Course 1 Basic Operations I", The Chemical Society of Japan, 4th Edition, Maruzen Co., Ltd., Apr. 5, 1996, pp. 184-189.

* cited by examiner

JAK INHIBITORS HAVING A SPECIFIC PARTICLE SIZE DISTRIBUTION

TECHNICAL FIELD

The present disclosure relates to 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution, to pharmaceutical compositions and processes for preparing the same, and to methods of using the same, for example, for the treatment of dermatological conditions.

BACKGROUND

International Application Publication WO/2009/114512 discloses certain JAK inhibitors, including the compound 2-(3-(4-(7H-pyrrolo[2,3-d]pyrimidin-4-yl)-1H-pyrazol-1-yl)-1-(cyclopropylsulfonyl)azetidin-3-yl)acetonitrile, its preparation as a trifluoroacetic acid salt, and as a phosphoric acid salt.

SUMMARY

There is a need for 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution which can be effectively, safely, and reproducibly used, and for methods for preparation and purification which can be used efficiently and reproducibly on a large scale for industrial manufacture. In particular, there is a need for crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution which can be effectively, safely, and reproducibly used, and for methods for preparation and purification which can be used efficiently and reproducibly on a large scale for industrial manufacture. More particularly, there is a need for substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile which can be effectively, safely, and reproducibly used, and for methods for preparation and purification which can be used efficiently and reproducibly on a large scale for industrial manufacture.

In certain embodiments, the present disclosure provides a substantially polymorphically pure crystalline form I 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution and processes for making the same. In certain preferred embodiments, the present disclosure provides a substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl) acetonitrile having a specific particle size distribution and processes for making the same. In certain embodiments, the present disclosure provides a substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution and processes for making the same.

In certain embodiments, the present disclosure provides a pharmaceutical composition comprising a substantially polymorphically pure form I 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution and a pharmaceutically acceptable excipient. In certain preferred embodiments, the present disclosure provides a pharmaceutical composition comprising a substantially polymorphically pure form II 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution and a pharmaceutically acceptable excipient. In certain embodiments, the present disclosure provides a pharmaceutical composition comprising a substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution and a pharmaceutically acceptable excipient.

In certain embodiments, the present disclosure provides a method of treating a dermatological condition comprising administering to a non-human mammal in need thereof an effective amount of the substantially polymorphically pure form I 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution. In certain preferred embodiments, the present disclosure provides a method of treating a dermatological condition comprising administering to a non-human mammal in need thereof an effective amount of the substantially polymorphically pure form II 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution. In certain embodiments, the present disclosure provides a method of treating a dermatological condition comprising administering to a non-human mammal in need thereof an effective amount of the substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution.

The present disclosure provides tablets comprising 2-(3-(4-(7H-pyrrolo[2,3-d]pyrimidin-4-yl)-1H-pyrazol-1-yl)-1(cyclopropylsulfonyl)azetidin-3-yl)acetonitrile as described herein, wherein the tablets have a specific acceptance value such as about 5 or lower.

The present disclosure provides a process for making 2-(3-(4-(7H-pyrrolo[2,3-d]pyrimidin-4-yl)-1H-pyrazol-1-yl)-1(cyclopropylsulfonyl)azetidin-3-yl)acetonitrile having a specific particle size distribution such as d50 of 15-30 μm, a d90 of 50-80 μm, a dv90 of ≤80 μm, and a dv50 of ≤30 μm.

DESCRIPTION

The present disclosure relates to a compound, 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific particle size distribution, polymorphs thereof identified herein as form I, form II, and form III and pharmaceutical compositions thereof and methods of using the polymorphs, for example, for the treatment of dermatological conditions, methods of making the polymorphs, and methods of making the compound and intermediates thereof.

Crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile having a specific PSD (particle size distribution) and/or a certain Acceptance Value (AV) can provide various processing advantages (e.g., good flow characteristics, e.g., to provide weight and content uniformity of tablets) or therapeutic advantages (e.g., favorable PK in vivo profile). More specifically, form II 2-(3-(4-(7H-pyrrolo[2,3-d]pyrimidin-4-yl)-1H-pyrazol-1-yl)-1-(cyclopropylsulfonyl)azetidin-3-yl)acetonitrile as described herein can provide various processing advantages (e.g., good flow characteristics), product advantages (e.g., to provide weight and/or content uniformity of tablets), or therapeutic advantages (e.g., favorable PK in vivo profile).

1. DEFINITIONS

Unless otherwise defined, all technical and scientific terms used herein have the same meaning as commonly understood by one of ordinary skill in the art. In case of conflict, the present document, including definitions will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "about" when used in connection with a measurable numerical variable, refers to the indicated value of the variable and to all values of the variable that are within the experimental error of the indicated value or within ±10 percent of the indicated value, whichever is greater.

The term "acceptable excipient" refers to those typically used in preparing veterinary and pharmaceutical compositions and should be pure and non-toxic in the amounts used. They generally are a solid, semi-solid, or liquid material which in the aggregate can serve as a vehicle or medium for the active ingredient. Some examples of acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The term "aromatic solvent" refers to a benzene optionally substituted with one or two substituents selected from the group consisting of methyl, chloro, bromo, cyano, nitro, aceto. The term "aromatic solvent" specifically includes, nitrobenzene, chlorobenzene, toluene, xylene, and acetophenone.

The term "$C_{1-5}$ alcohol" refers to a straight or branched alkanol having from one to five carbon atoms, for example methanol, ethanol, n-propanol, iso-propanol, 1-butanol, ethylene glycol, 1,3-propanediol, and the like.

The term "$C_1$-$C_4$ alkyl" refers to a straight or branched alkyl chain having from one to four carbon atoms and includes methyl, ethyl, propyl, isopropyl, butyl, and the like.

The term "$C_{2-8}$ alkyl ether" refers to a straight, branched, or cyclic alkyl ether having a total of from two to eight carbon atoms, for example dimethyl ether, diethyl ether, methyl t-butyl ether, THF, 2-methyl THF, dioxane, and the like.

The term "$C_{3-8}$ alkyl acetate" refers to straight or branched alkyl esters of acetic acid having a total of three to eight carbons, for example, methyl acetate, ethyl acetate, isopropyl acetate, butyl acetate, isobutyl acetate, and the like.

The term "$C_{2-5}$ alkyl cyanide" refers to straight or branched alkyl cyanides having a total of two to five carbon atoms, for example acetonitrile, propionitrile, and butyronitrile.

The term "$C_{3-9}$ alkyl ketone" refers to a straight, branched, or cyclic alkyl group having an oxo group and having a total of from three to nine carbon atoms, for example acetone, methyl ethyl ketone, and cyclohexanone.

The term "$C_{5-6}$ hydrocarbon" refers to a straight, branched, or cyclic saturated alkyl hydrocarbon, for example, pentane, hexane, heptane, octane, cyclopentane, cyclohexane, methyl cyclohexane and the like.

The term "5-6 membered heterocyclic ring" refers to a 5 to 6 membered monocyclic saturated ring that includes the oxygen atoms to which $R_1$ and $R_2$ are attached and boron to which those oxygen atoms are attached.

The terms "crystallize," "crystallizing," "crystallization," and the like refer to complete dissolution followed by precipitation and slurry processes that do not involve complete dissolution. Slurry processes include those that encompass continuation of the crystallization process following precipitation after complete dissolution.

The term "d50" or "dv50" is known as the median diameter or the medium value of the particle size distribution, it is the value of the particle diameter at 50% in the cumulative distribution, measured for example by a light scattering method such as by a Malvern Mastersizer or a Helos laser diffractometer from Sympatec. For example, if d50=10 μm, then 50% of the particles in the sample are larger than 10 μm, and 50% are smaller than 10 μm.

The term "d90" or "dv90" is the value of the particle diameter at 90% in the cumulative distribution, measured for example by a light scattering method such as by a Malvern Mastersizer or a Helos laser diffractometer from Sympatec. For example, if d90=10 μm, then 90% of the particles in the sample are smaller than 10 μm.

The term "dermatological conditions" includes skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions.

The term "effective amount" refers to the amount or dose of compound of the invention, or a pharmaceutically acceptable salt thereof which, upon single or multiple dose administration to the patient, provides the desired effect in the patient under diagnosis or treatment. An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient or non-human mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The terms "patient," "subject," and "non-human mammal" refers to a warm-blooded animal, such as dogs, cats, mice, rats, guinea pigs, rabbits, cows, horses, sheep, goats, and pigs. Particular non-human mammals are pets or companion animals, such as dogs and cats and also mice, guinea pigs, and rabbits. Preferred non-human mammals are dogs and cats. Preferably, the non-human mammal is a canine. A particularly preferred non-human mammal is the dog.

The term "salt" refers to salts of veterinary or pharmaceutically acceptable organic acids and bases or inorganic acids and bases. Such salts are well known in the art and include those described in Journal of Pharmaceutical Science, 66, 2-19 (1977). An example is the hydrochloride salt. The term as used herein expressly excludes a trifluoroacetic acid salt and a phosphoric acid salt.

The term "substantially polymorphically pure" refers to greater than 90%, preferably greater than 97%, more preferably greater than 99%, and even more preferably greater than 99.5% polymorphic purity.

The terms "treating" or "to treat" refer to restraining, slowing, stopping, or reversing the progression or severity of an existing symptom or disorder.

The term "water activity" is equal to p/p* where p is the partial vapor pressure of water in the solution, and p* is the partial vapor pressure of pure water at the same temperature.

For the recitation of numeric ranges herein, each intervening number there between with the same degree of precision is explicitly contemplated. For example, for the range of 92-97, the numbers 93, 94, 95, and 96 are contemplated in addition to 92 and 97, and the number 92.1, 92.2, 92.3, 92.4, 92.5, 92.6 et cetera to 97.0 are explicitly contemplated to be within the range.

The present disclosure makes reference to certain embodiments or aspects. However, it is within the scope of this disclosure that the various characteristics of the embodiments and/or aspects may be combined together along with any characteristics disclosed in the rest of the description, examples, claims, etc.

2. COMPOUNDS

Compounds of the invention include crystalline forms I, II, and III of 2-(3-(4-(7H-pyrrolo[2,3-d]pyrimidin-4-yl)-1H-pyrazol-1-yl)-1-(cyclopropylsulfonyl)azetidin-3-yl)acetonitrile. Crystalline forms of 2-(3-(4-(7H-pyrrolo[2,3-d]pyrimidin-4-yl)-1H-pyrazol-1-yl)-1-(cyclopropylsulfonyl)azetidin-3-yl)acetonitrile are desired to provide for efficiency and reproducibility of production of pharmaceutical formulations and for pharmaceutical compositions with suitable stability.

2-(3-(4-(7H-pyrrolo[2,3-d]pyrimidin-4-yl)-1H-pyrazol-1-yl)-1-(cyclopropylsulfonyl)azetidin-3-yl)acetonitrile is also known by the names 2-[1-cyclopropylsulfonyl-3-[4-(7H-pyrrolo[2,3-d]pyrimidin-4-yl)pyrazol-1-yl]azetidin-3-yl]acetonitrile and 2-(1-cyclopropylsulfonyl-3-pyrazol-1-yl-(4-(7H-pyrrolo[2,3-d]pyrimidin azetidin-3-yl)acetonitrile and for clarity is the compound of the formula (I), below:

(I)

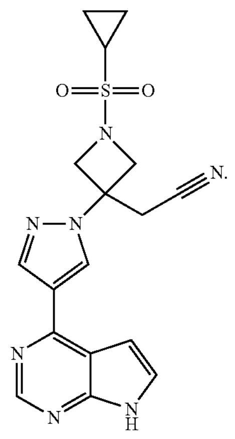

In a preferred embodiment, a compound of the invention is crystalline form I 2-(3-(4-(7H-pyrrolo[2,3-d]pyrimidin-4-yl)-1H-pyrazol-1-yl)-1-(cyclopropylsulfonyl)azetidin-3-yl) acetonitrile as described herein. Crystalline form I 2-(3-(4-(7H-pyrrolo[2,3-d]pyrimidin-4-yl)-1H-pyrazol-1-yl)-1-(cyclopropylsulfonyl)azetidin-3-yl)acetonitrile is an anhydrate.

In another preferred embodiment, a compound of the invention is crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile as described herein. Crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile is also an anhydrate.

In another preferred embodiment, a compound of the invention is crystalline form III 2-(3-(4-(7H-pyrrolo[2,3-d]pyrimidin-4-yl)-1H-pyrazol-1-yl)-1-(cyclopropylsulfonyl)azetidin-3-yl)acetonitrile as described herein. Crystalline form III 2-(3-(4-(7H-pyrrolo[2,3-d]pyrimidin-4-yl)-1H-pyrazol-1-yl)-1-(cyclopropylsulfonyl)azetidin-3-yl)acetonitrile is a hydrated form.

Forms I, II, and III as well as other polymorphic forms of 2-(3-(4-(7H-pyrrolo[2,3-d]pyrimidin-4-yl)-1H-pyrazol-1-yl)-1-(cyclopropylsulfonyl)azetidin-3-yl)acetonitrile can be characterized by X-ray diffraction. The peaks were measured using a powder diffractometer equipped with a copper source, primary beam monochromator, and position sensitive detector. The incident beam was collimated using a 1° divergence slit. The source was operated at 40 kV and 40 mA. X-ray powder diffraction data were collected from 2.5 degrees to 50 degrees using a step width of 0.02 degree and a 37 second step time. Alternately, peaks were measured using a powder diffractometer equipped with a copper source, primary beam monochromator, and position sensitive detector. The incident beam was collimated using a 1° divergence slit. The source was operated at 40 kV and 40 mA. X-ray powder diffraction data were collected from 1.5 degrees to 50 degrees using a step width of 0.02 degree and a 12 second step time.

It is recognized that the relative intensity of X-ray powder diffraction peaks can be dependent on preferred orientation and other factors such as particle size and sample preparation. Where the effects of preferred orientation and/or particle size are present, peak intensities may be altered, but the characteristic peak positions of the polymorph are unchanged. See, e.g., The United States Pharmacopoeia #24, National Formulary #19, pages 1843-1844, 2000. Therefore, a sample of form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile may require processing to mitigate such factors, such as grinding the sample in an agate mortar and pestle or other measures. It is understood that differences in relative intensity of the diffraction peaks does not preclude an acquired pattern from being consistent with form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile.

Furthermore, it is also well known in the crystallography art that, for any given crystal form, the angular peak positions may vary slightly. For example, peak positions can shift due to sample displacement or a variation in the temperature or relative humidity at which a sample is analyzed. In the present case, a peak position variability of ±0.2° in 2θ will take into account these potential variations without hindering the unequivocal identification of the crystalline form of the present disclosure.

Form I, II, or III 2-(3-(4-(7H-pyrrolo[2,3-d]pyrimidin-4-yl)-1H-pyrazol-1-yl)-1-(cyclopropylsulfonyl)azetidin-3-yl)acetonitrile can also be characterized by differential scanning calorimetry. DSC can be carried out in closed (hermetically sealed) gold crucibles or aluminum pans with a pinhole; sample filled under ambient conditions or $N_2$ flow (for 3-10 minutes); heating rate of 10° C./minute from −50° C. to 300° C.

Form I

Crystalline form I 2-(3-(4-(7H-pyrrolo[2,3-d]pyrimidin-4-yl)-1H-pyrazol-1-yl)-1-(cyclopropylsulfonyl)azetidin-3-yl)acetonitrile was found to have the following characteristic peaks in degrees 2-theta (°2θ) having (relative intensity of greater than about 10% of the largest peak, $I_o/I_{100}$%): 12.72° (43.1%), 14.04° (61.3%), 17.56° (20.8%), 20.33° (87.4%), 24.50° (100%), and 25.83° (94.9%) (±0.2° 2θ).

The present disclosure provides a substantially polymorphically pure form I 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 12.72°, 14.04°, 17.56°, 20.33°, 24.50°, or 25.83° 2θ (±0.2° 2θ). More particularly, the present disclosure provides substantially polymorphically pure form I 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 12.72° and 24.50° (±0.2° 2θ) or comprising peaks at 20.33° and 24.50° (±0.2° 2θ) or comprising peaks at 12.72° and 20.33° (±0.2° 2θ).

As used herein, the term "form I 2-(3-(4-(7H-pyrrolo[2,3-d]pyrimidin-4-yl)-1H-pyrazol-1-yl)-1-(cyclopropylsulfonyl)azetidin-3-yl)acetonitrile" includes the term "substantially polymorphically pure form I 2-(3-(4-(7H-pyrrolo[2,3-d]pyrimidin-4-yl)-1H-pyrazol-1-yl)-1-(cyclopropylsulfonyl)azetidin-3-yl)acetonitrile."

Form II

Crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile was found to have the following characteristic peaks in degrees 2-theta (°2θ) having (relative intensity of greater than about 10% of the largest peak, $I_o/I_{100}$%): 5.34° (16.2%); 10.68° (26.2%); 14.26° (20.8%); 16.06° (13.5%); 16.39° (17.9%); 16.48° (18.6%); 18.26° (19.5%); 18.65° (43.4%); 19.03° (100.0%); 21.05° (10.2%); 21.15° (9.9%); 21.45° (9.0%); 21.76° (20.5%); 22.45° (9.6%); 22.68° (22.5%); 23.23° (11.1%); 23.72° (12.3%); 24.90° (11.7%); 25.08° (9.2%); 26.75° (30.7%); and 31.18° (10.1%); (±0.2° 2θ).

The present disclosure provides a substantially polymorphically pure form II 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 5.34°, 10.68°, 14.26°, 16.06°, 16.39°, 16.48°, 18.26°, 18.65°, 19.03°, 21.05°, 21.76°, 22.68°, or 26.75° (±0.2° 2θ). More particularly, the present disclosure provides substantially polymorphically pure form II 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 18.65° and 10.68° (±0.2° 2θ) or comprising peaks at 18.65° and 21.760 (0.1° 2θ) or comprising peaks at 18.65° and 22.68° (0.1° 2θ) or comprising peaks at 26.750 and 21.760 (±0.2° 2θ).

As used herein, the term "form II 2-(3-(4-(7H-pyrrolo[2,3-d]pyrimidin-4-yl)-1H-pyrazol-1-yl)-1-(cyclopropylsulfonyl)azetidin-3-yl)acetonitrile" includes the term "substantially polymorphically pure form II 2-(3-(4-(7H-pyrrolo[2,3-d]pyrimidin-4-yl)-1H-pyrazol-1-yl)-1-(cyclopropylsulfonyl)azetidin-3-yl)acetonitrile."

Form III

Crystalline form III 2-(3-(4-(7H-pyrrolo[2,3-d]pyrimidin-4-yl)-1H-pyrazol-1-yl)-1-(cyclopropylsulfonyl)azetidin-3-yl)acetonitrile was found to have the following characteristic peaks in degrees 2-theta (°2θ) having (relative intensity of greater than about 10% of the largest peak, $I_o/I_{100}$%): 11.080 (62.3%); 12.320 (15.9%); 13.280 (13.7%); 14.060 (15.3%); 14.730 (32.8%); 17.860 (16.9%); 18.060 (46.4%); 18.270 (18.1%); 18.510 (35.2%); 18.910 (10.9%); 20.360 (15.8%); 21.480 (12.7%); 22.240 (26.9%); 22.690 (100%); 23.400 (10.2%); 24.760 (18.8%); 25.480 (55.4%); 25.970 (12.6%); 26.700 (12.5%); and 28.040 (12.8%); (±0.2° 2θ).

The present disclosure provides a substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 11.08°, 14.73°, 18.06°, 18.27°, 18.510, 22.24°, 22.69°, 24.76°, 25.48°, or 28.040 (±0.2° 2θ). More particularly, the present disclosure provides substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 11.080 and 22.69°; (±0.2° 2θ) or comprising peaks at 14.730 and 22.690 (±0.2° 2θ) or comprising peaks at 22.690 and 25.480 (±0.2° 2θ) or comprising peaks at 11.080 and 18.060 (±0.2° 2θ) or comprising peaks at 11.080 and 25.480 (±0.2° 2θ).

As used herein, the term "form III 2-(3-(4-(7H-pyrrolo[2,3-d]pyrimidin-4-yl)-1H-pyrazol-1-yl)-1-(cyclopropylsulfonyl)azetidin-3-yl)acetonitrile" includes the term "substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile."

The skilled artisan will appreciate that compounds may exist as tautomers. All tautomeric forms the compounds of the invention are contemplated to be within the scope of the present disclosure.

Compounds of the invention also include all isotopic variations, in which at least one atom of the predominant atom mass is replaced by an atom having the same atomic number, but an atomic mass different from the predominant atomic mass. Use of isotopic variations (e.g., deuterium, $^2H$) may afford greater metabolic stability. Additionally, certain isotopic variations of the compounds of the invention may incorporate a radioactive isotope (e.g., tritium, $^3H$, or $^{14}C$), which may be useful in drug and/or substrate tissue distribution studies. Substitution with positron emitting isotopes, such as $^{11}C$, $^{18}F$, $^{15}O$ and $^{13}N$, may be useful in Positron Emission Topography (PET) studies.

3. PROCESSES TO MAKE CRYSTALLINE FORMS

Form I Processes

Crystalline form I 2-(3-(4-(7H-pyrrolo[2,3-d]pyrimidin-4-yl)-1H-pyrazol-1-yl)-1-(cyclopropylsulfonyl)azetidin-3-yl)acetonitrile may be prepared by crystallization under controlled conditions. The present disclosure also provides a process for making substantially polymorphically pure crystalline form I 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from a mixture of acetone and heptane as an anti-solvent. In a preferred embodiment, form I 2-(3-(4-(7H-pyrrolo[2,3-d]pyrimidin-4-yl)-1H-pyrazol-1-yl)-1-(cyclopropylsulfonyl)azetidin-3-yl) acetonitrile can also be obtained by dehydration of Form III samples, typically be heating at temperatures of from about 40° C. to about 80° C. under vacuum.

Form II Processes

Crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile may be prepared by crystallization under controlled conditions by crystallization from a solvent or a mixture of solvents. The present disclosure also provides a process for making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from a solvent or a mixture of solvents further containing water and having a water activity of less than 0.7. In practice suitable solvents are selected from the group consisting of $C_{1-5}$ alcohol, $C_{2-8}$ alkyl ether, $C_{2-8}$ alkyl acetate, $C_{2-5}$ alkyl cyanide, $C_{3-9}$ alkyl ketone, and aromatic solvent; each having a water activity of less than about 0.7.

In a preferred embodiment, the present disclosure also provides a process for making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from a solvent or a mixture of solvents further containing water and having a water activity of less than 0.5.

The use of an anti-solvent may be advantageous. As used in this context an "anti-solvent" refers to a solvent in which 2-(3-(4-(7H-pyrrolo[2,3-d]pyrimidin-4-yl)-1H-pyrazol-1-yl)-1-(cyclopropylsulfonyl)azetidin-3-yl)acetonitrile is significantly less soluble relative to the selected solvent(s). Preferably, when an anti-solvent is used it is miscible with the selected solvent. While anti-solvents may be used, care must be taken that the selected anti-solvent(s) does not increase the water activity above the desired level.

It is understood that the water activity that provides substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile is temperature dependent. Higher temperatures of the final state of the crystallization can tolerate higher water activity. Thus, a water activity of about 0.7 is effective at temperatures of the final state of the crystallization of greater than about 40° C.

Because recoveries may be higher at lower temperatures, in a preferred embodiment, the present disclosure also provides a process for making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from a solvent or a mixture of solvents having a water activity of less than 0.5. Typically, a water activity of about 0.5 is effective at temperatures of the final state of the crystallization of less than about 25° C.

Preferred solvents are selected from the group consisting of $C_{1-5}$ alcohol and $C_{2-5}$ alkyl cyanide; each having a water activity of less than about 0.7. An even more preferred solvent is selected from the group consisting of $C_{1-5}$ alcohol and $C_{2-5}$ alkyl cyanide; each having a water activity of less than about 0.5.

In an embodiment, the present disclosure provides a process of making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from acetonitrile further comprising water having a water activity of less than 0.7.

In another embodiment, the present disclosure provides a process of making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from acetonitrile further comprising water having a water activity of less than 0.5.

The present disclosure provides a process of making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from acetonitrile further comprising water. Care must be taken to avoid the formation of undesired hydrated crystalline forms. Thus, preferred embodiments for crystallizing from acetonitrile further comprising water utilize a v/v ratio of 92-97 acetonitrile to 8-3 water; more preferred, crystallizing from acetonitrile further comprising water in a v/v ratio of 95-97 acetonitrile to 5-3 water. The use of 96:4 (v/v) acetonitrile/water has been found in practice to have a most favorable volume efficiency at temperatures below about 20° C.

Thus, an even more preferred process for making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile comprises, crystallizing from acetonitrile further comprising water in a v/v ratio of about 96 acetonitrile to about 4 water.

Optionally, the crystallization may be seeded with form II 2-(3-(4-(7H-pyrrolo[2,3-d]pyrimidin-4-yl)-1H-pyrazol-1-yl)-1-(cyclopropylsulfonyl)azetidin-3-yl)acetonitrile.

Crystallization by precipitation from a solution and slurrying techniques are contemplated to be within the scope of the present process. Where the crystallization involves complete dissolution, slow cooling is preferred at rates of between 0.2° C./minute and 0.02° C./minute. Crystallization to give form II does not require complete dissolution. Slurry processes can be used. A slurry can be formed by processing without complete dissolution or by complete dissolution followed by processing after initial precipitation. In a slurry process the volume should be sufficient to provide free-flowing slurry. The volume of solvent is not critical but should be kept to a minimal amount as a matter of convenience. The water activity of the solvent(s) used must take into account water including water that may be released from a hydrated starting material. Optionally, a slurry crystallization process may be seeded with form II 2-(3-(4-(7H-pyrrolo[2,3-d]pyrimidin-4-yl)-1H-pyrazol-1-yl)-1-(cyclopropylsulfonyl)azetidin-3-yl)acetonitrile.

In one embodiment non-form II containing 2-(3-(4-(7H-pyrrolo[2,3-d]pyrimidin-4-yl)-1H-pyrazol-1-yl)-1-(cyclopropylsulfonyl)azetidin-3-yl)acetonitrile is crystallized by slurry at temperature of about 50° C. or higher and optional cooling to recover the final product. In another embodiment non-form II 2-(3-(4-(7H-pyrrolo[2,3-d]pyrimidin-4-yl)-1H-pyrazol-1-yl)-1-(cyclopropylsulfonyl)azetidin-3-yl)acetonitrile is crystallized by slurry from a solvent at temperature of about room temperature. Optionally, the crystallization may be seeded with form II 2-(3-(4-(7H-pyrrolo[2,3-d]pyrimidin-4-yl)-1H-pyrazol-1-yl)-1-(cyclopropylsulfonyl)azetidin-3-yl)acetonitrile. Such slurry processes generally require 2 to 14 days.

Form III Processes

Crystalline form III 2-(3-(4-(7H-pyrrolo[2,3-d]pyrimidin-4-yl)-1H-pyrazol-1-yl)-1-(cyclopropylsulfonyl)azetidin-3-yl)acetonitrile may be prepared by crystallization under controlled conditions by crystallization from a solvent or a mixture of solvents. The present disclosure also provides a process for making substantially polymorphically pure crystalline form III 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from a solvent or a mixture of solvents further containing water and having a water activity of greater than 0.9. In practice suitable solvents are selected from the group consisting of water, $C_{1-5}$ alcohol, $C_{2-8}$ alkyl acetate, $C_{2-5}$ alkyl cyanide, and $C_{3-9}$ alkyl ketone; each having a water activity of greater than about 0.9.

The use of an anti-solvent may be advantageous. As used in this context an "anti-solvent" refers to a solvent in which 2-(3-(4-(7H-pyrrolo[2,3-d]pyrimidin-4-yl)-1H-pyrazol-1-yl)-1-(cyclopropylsulfonyl)azetidin-3-yl)acetonitrile is significantly less soluble relative to the selected solvent(s). Preferably, when an anti-solvent is used it is miscible with the selected solvent.

While anti-solvents may be used, care must be taken that the selected anti-solvent(s) does not decrease the water activity below the desired level.

A preferred solvent is selected from the group consisting of $C_{1-5}$ alcohol having a water activity of greater than about 0.9.

Crystallization from a solution and slurrying techniques are contemplated to be within the scope of the present process. Where the crystallization involves complete dissolution, slow cooling is preferred at rates of between 0.2° C./minute and 0.02° C./minute. Crystallization to give form III does not require complete dissolution. Slurry processes can be used. A slurry can be formed by processing without complete dissolution or by complete dissolution followed by processing after initial precipitation. In a slurry process the volume should be sufficient to provide free-flowing slurry. The volume of solvent is not critical but should be kept to a minimal amount as a matter of convenience. Optionally, a slurry crystallization process may be seeded with form III 2-(3-(4-(7H-pyrrolo[2,3-d]pyrimidin-4-yl)-1H-pyrazol-1-yl)-1-(cyclopropylsulfonyl)azetidin-3-yl)acetonitrile.

In one embodiment non-form III containing 2-(3-(4-(7H-pyrrolo[2,3-d]pyrimidin-4-yl)-1H-pyrazol-1-yl)-1-(cyclopropylsulfonyl)azetidin-3-yl)acetonitrile is crystallized by slurry from a solvent having a water activity greater than 0.9 at temperature of about room temperature. Optionally, the crystallization may be seeded with form III 2-(3-(4-(7H-pyrrolo[2,3-d]pyrimidin-4-yl)-1H-pyrazol-1-yl)-1-(cyclopropylsulfonyl)azetidin-3-yl)acetonitrile. Such slurry processes generally require 2 to 10 days.

Care must be taken when drying form III 2-(3-(4-(7H-pyrrolo[2,3-d]pyrimidin-4-yl)-1H-pyrazol-1-yl)-1-(cyclopropylsulfonyl)azetidin-3-yl)acetonitrile to avoid conversion to form I, preferably under vacuum at temperatures below 20° C.

4. SYNTHETIC METHODS

The present disclosure provides a process for making 2-(3-(4-(7H-pyrrolo[2,3-d]pyrimidin-4-yl)-1H-pyrazol-1-yl)-1-(cyclopropylsulfonyl)azetidin-3-yl)acetonitrile as depicted in Scheme A.

Scheme A

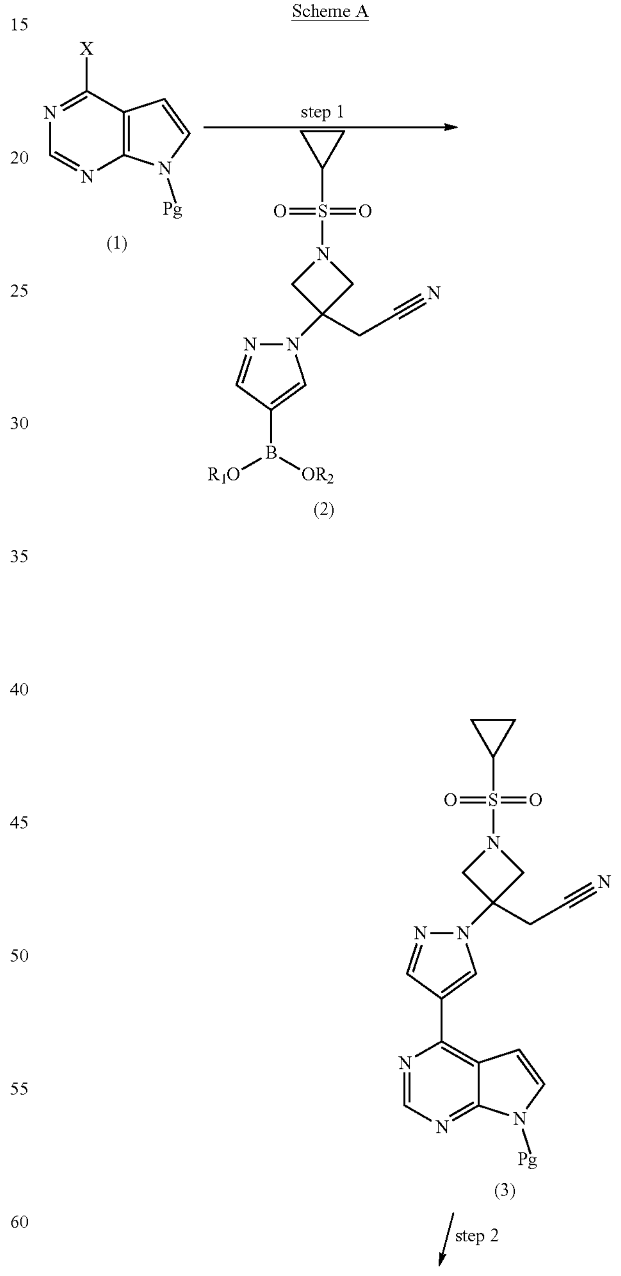

-continued

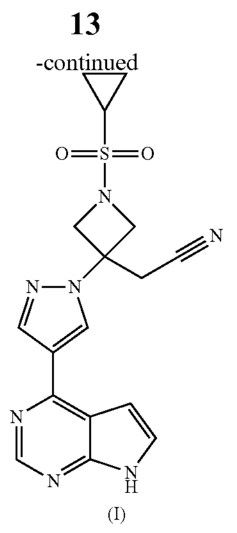

(I)

In Scheme A, step 1, a compound of formula (1) is reacted with a compound of formula (2) in the presence of a suitable catalyst to give a compound of formula (3). A compound of formula (1) is one wherein X is selected from the group consisting of tosylate, triflate, chloro, bromo, and iodo and Pg is a protecting group. In practice a compound of formula (1) wherein X is bromo or chloro are preferred and chloro is even more preferred. A variety of protecting groups are suitable. The selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999). For example, t-BOC, 2-(trimethylsilyl)ethoxymethyl, and N-pivaloyloxymethyl are useful, to mention only a few. In practice, a t-BOC group is preferred. A compound of formula (2) is one wherein $R_1$ and $R_2$ are independently selected from the group consisting of hydrogen and $C_{1-6}$ alkyl; or $R_1$ and $R_2$, together with the oxygen atoms to which they are attached and the boron atom, form a 5- to 6-membered heterocyclic ring, which is optionally substituted with 1, 2, 3, or 4 $C_{1-4}$ alkyl groups. As will be appreciated by the skilled person the depicted reaction in step 1 is the well-known Suzuki reaction. A variety of suitable catalysts are available. Both nickel and palladium catalysts are useful, however, palladium catalysts are preferred. A number of suitable palladium(0) and palladium(II) catalysts are known in the art. For example, tetrakis(triphenylphosphine)palladium(0), tetrakis(triphenylphosphine)palladium(II)chloride, 4,5-bis(diphenylphosphino)-9,9-dimethylxanthene, and dichloromethane [1,1'-bis(diphenylphosphino)ferrocene]dichloropalladium(II) (1:1).

The reaction is typically carried out in a solvent, including a large variety of organic solvents. The solvent may contain water. For example, suitable solvents include 1,4-dioxane, THF, 1-butanol, 1,2-dimethoxyethane (DME), 2-propanol, toluene, or ethanol, or a combinations thereof. Typical palladium catalyst is used in amounts from about 0.01 to about 0.1 equivalents.

The reaction is carried out in the presence of base. Both organic and inorganic bases can be used, for example, alkali metal carbonates and alkali metal bicarbonates as well as bases such as cesium carbonate are used. The reaction is typically conducted at a temperature of about 40° C. to about 100° C. and generally requires 1 to 18 hours.

The desired particle size for the filtered and dried compound (I) from step 2 of Scheme A may be achieved using, for example, a loop-style jet-mill. The jet-milling may, for example, be performed under nitrogen with venturi and mill pressures of 10 psi and a material feed rate of 9.0-9.6 kg/hr.

5. COMPOSITIONS

The present disclosure provides a composition comprising 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof. The compositions may comprise particles of the compound, wherein said particles in the composition have a specific particle size distribution.

The present compounds provide therapeutic benefits even at low doses. It is problematic to uniformly distribute the small amount of the compound in unit dose forms. This is particularly an issue when, for example, the unit dose form may be further divided such as may be the case when treating a smaller animal. It has surprisingly been found that the present compound may be effectively dispersed within a unit dose form by the methods described herein, such as, for example, controlling the PSD.

Uniformity of dosage units may be assessed according to the United States Pharmacopeia <905>. The results are expressed in Acceptance Value (AV). The present disclosure provides an oral unit dose form, such as a tablet, comprising the present compounds. The tablet may comprise other substances as outlined herein. The tablet may be coated as described herein. The present tablets have an AV of about 5 or lower, about 4.5 or lower, about 4 or lower, about 3.5 or lower, about 3 or lower.

The present tablets may be assayed via an UHPLC-UV method by isocratic elution for the purposes of calculating the AV according to the following method. Note, the materials and equipment are mentioned as examples. Items of similar quality may be used.

| Reagents | |
|---|---|
| Name | Quality |
| Acetonitrile | HPLC grade |
| Water for chromatography | HPLC grade |
| Water purified | Ph. Eur. |
| Phosphoric Acid | 85% (w/w), p.a. |

| Reference substances | | |
|---|---|---|
| Name | Quality | Supplier (Source) |
| Form II* | n.a. (assay of content certified) | Elanco Animal Health Inc. |

*Form II 2-(3-(4-(7H-pyrrolo[2,3-d]pyrimidin-4-yl)-1H-pyrazol-1-yl)-1-(cyclopropylsulfonyl)azetidin-3-yl)acetonitrile The following pieces of equipment are mentioned as examples. Equipment of similar quality provided by other suppliers may also be used.

Equipment

| Name | Supplier | Type |
|---|---|---|
| UHPLC | Agilent Technologies | 1290 Infinity Series with 40 μL injection loop |

All solutions can be adjusted as long as concentrations are maintained.

1. Mobile phase buffer: 0.1% phosphoric acid, pH 3.0
2. Mobile phase: 20% acetonitrile in mobile phase buffer.
3. Diluent: 90% acetonitrile in water
4. Working standard solution for Content Uniformity—Prepare a solution of 6.0 μg/mL Form II reference substance in mobile phase buffer.

Sample Solutions

Prepare for 10 units.

1. Select flask sizes according to Table A.

TABLE A

Flask Size for Content Uniformity sample preparation

| Strength (mg) | 2.4 | 3.6 | 4.8 | 5.4 | 6.4 | 8.5 | 15 | 16 |
|---|---|---|---|---|---|---|---|---|
| Flask Size (mL) | 20 | 25 | 50 | 50 | 50 | 50 | 50 | 50 |
| Flask Size for further dilution (mL) | 20 | 25 | 20 | 20 | 20 | 25 | 50 | 50 |
| Final concentration of API (μg/mL) | 6.0 | 5.76 | 4.8 | 5.4 | 6.4 | 6.8 | 6.0 | 6.4 |

2. Place one tablet into the flask.
3. Add about 10% of the volume of the flask of water. Sonicate until complete disintegration of the tablet.
4. Add additional 70% of acetonitrile and sonicate.
5. After cooling to room temperature, dilute to volume with acetonitrile
6. Transfer 1.0 mL of this stock sample solution into a volumetric flask of the corresponding size (see Table A) and dilute to volume with Mobile Phase Buffer.
7. Filter an aliquot into a HPLC vial (working sample solution).
8. Inject in HPLC system HPLC Method Parameters Column: Agilent Zorbax Eclipse Plus-C8, 50×2.1 mm, 1.8 μm Column temperature: 40° C.

Total flow rate: 0.4 mL/min

Injection volume: 3.0 μL

Detection wavelength: 225 nm

Runtime: 3.0 min

Autosampler temperature: not controlled/room temperature

Needle wash solution: acetonitrile/water for chromatography 70/30 (v/v)

Separation type: isocratic

Typical retention times: Form II—1.4 min

Calculations

Assess the content of Form II in % of declared content.

Perform the calculation of content uniformity according to USP <905> for the 10 individual units.

The present disclosure provides a composition comprising particles of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof, wherein said particles in the composition have a particle size distribution characterized by a d50 of 15-30 μm, a d90 of 50-80 μm, a dv90 of ≤80 μm, and a dv50 of ≤30 μm.

Compositions comprising particles of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof, wherein said particles in the composition have a specified particle size distribution can be prepared by methods known in the art (e.g., the size reduction or micronization of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof may be carried out by using any of the conventional mills, such as wet mills, jet mills, ball mills, colloid mills, grinding mills, roller mills, impact mills, or cryo-mills, preferred are wet mills and jet mills). In certain embodiments, 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof may be wet-milled in any suitable aqueous, non-aqueous or organic solvent (e.g. an oil). In certain embodiments, 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof may be dry-milled. In certain embodiments, 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof may be jet-milled.

6. PHARMACEUTICAL COMPOSITIONS

The present compounds are usually administered in the form of compositions, that is, in admixture with at least one acceptable excipient. The proportion and nature of any acceptable excipient(s) are determined by the properties of the selected compound, the chosen route of administration, and standard practice as in the veterinary and pharmaceutical fields.

The present disclosure provides a pharmaceutical composition comprising 2-(3-(4-(7H-pyrrolo[2,3-d]pyrimidin-4-yl)-1H-pyrazol-1-yl)-1-(cyclopropylsulfonyl)azetidin-3-yl) acetonitrile or a salt thereof and an acceptable excipient or excipients. The composition may comprise particles of the compound having a particle size distribution of d50 of 15-30 μm, a d90 of 50-80 μm, a dv90 of ≤80 μm, and a dv50 of ≤30 μm. In a preferred embodiment, the present disclosure provides a pharmaceutical composition comprising particles of crystalline form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile and an acceptable excipient or excipients, wherein said particles in the composition have a particle size distribution of d50 of 15-30 μm, a d90 of 50-80 μm, a dv90 of ≤80 μm, and a dv50 of ≤30 μm. In another preferred embodiment, the present disclosure provides a pharmaceutical composition comprising particles of crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, and at least one acceptable excipient or excipients, wherein said particles in the composition have a particle size distribution of d50 of 15-30 μm, a d90 of 50-80 μm, a dv90 of ≤80 μm, and a dv50 of ≤30 μm. In another preferred embodiment, the present disclosure provides a pharmaceutical composition comprising particles of substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, and at least one acceptable excipient, wherein said particles in the composition have a particle size distribution of d50 of 15-30 μm, a d90 of 50-80 μm, a dv90 of ≤80 μm, and a dv50 of ≤30 μm.

The present compositions may be in the form of tablets comprising 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof. The tablets may have an AV of the 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof of 5 or lower, 4.5 or lower, 4 or lower, 3.5 or lower, 3 or lower.

In effecting treatment of a subject in need of such treatment, the present compositions can be administered in any form and route which makes the compound bioavailable.

The present compositions may be administered by a variety of routes, including orally, in particularly by tablets and capsules. Other routes of administration include parenteral routes, more particularly by inhalation, subcutaneously, intramuscularly, intravenously, intraarterially, transdermally, intranasally, rectally, vaginally, ocularly, topically, sublingually, and buccally, intraperitoneally, intraadiposally, intrathecally and via local delivery for example by catheter or stent.

One skilled in the art can readily select the proper form and route of administration depending upon the particular characteristics of the composition selected, the disorder or condition to be treated, the stage of the disorder or condition, and other relevant circumstances. The pharmaceutical compositions herein may be administered to the patient, for example, in the form of tablets, capsules, cachets, papers, lozenges, wafers, elixirs, ointments, transdermal patches, aerosols, inhalants, suppositories, drenches, solutions, and suspensions.

In one embodiment, the composition is adapted for oral administration, such as a tablet. In an embodiment, the composition is adapted for oral administration, such as chewable formulation, adapted for oral administration.

The present compositions may be prepared in a manner well known in the veterinary and pharmaceutical art and include at least one of the present compounds as the active ingredient. The amount of a compound of the present disclosure in the present compositions may be varied depending upon its particular form and may conveniently be between 1% to about 50% of the weight of the unit dose form. The present compositions are preferably formulated in a unit dose form, each dose typically containing from about 0.25 mg to about 20 mg of a compound of the invention. For example, from about 1 mg to about 20 mg, from about 2 mg to about 17 mg, from about 2.4 mg to about 15 mg. One or more unit dose form(s) may be taken to affect the treatment dosage.

The present compositions may be an oral dosage form. Preferably the comprising 2.4 mg, 3.6 mg, 4.8 mg, 5.4 mg, 6.4 mg, 8.5 mg, 15 mg, or 16 mg of the present. Preferred are oral dosage form comprising 4.8 mg, 6.4 mg, 8.5 mg, or 15 mg of the present compound having the specified AV and/or PSD.

The present oral dosage forms may be tablets. The present tablets are preferably coated. For example, the coating may be selected from commercially available coating mixes which are acceptable for the intended use herein. One preferred coating mix is Opadry™ available from Colorcon GmbH, Buchwiese 18 D-65510 Idstein, Germany.

The present compositions preferably comprise microcrystalline cellulose, pregelatinized starch, calcium phosphate dibasic dihydrate, povidone, magnesium stearate, coating, or any combination thereof. The present compositions preferably comprise pregelatinized starch.

7. METHODS OF USE

The present disclosure provides a method of treating dermatological conditions, comprising administering to a non-human mammal in need thereof an effective amount of a present compound or composition.

The present disclosure provides a method of treating dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions], comprising administering to a non-human mammal in need thereof an effective amount of a composition as disclosed herein. A preferred non-human mammal is a dog. In certain embodiments, the dog is at least 9 months of age, or at least 12 months of age.

In a preferred embodiment, the present disclosure provides a method of treating atopic dermatitis comprising administering to a non-human mammal in need thereof an effective amount of a composition as disclosed herein. A preferred non-human mammal is a dog. In certain embodiments, the dog is at least 9 months of age, or at least 12 months of age.

In a preferred embodiment, the present disclosure provides a method of treating pruritus associated with allergic dermatitis comprising administering to a non-human mammal in need thereof an effective amount of a composition as disclosed herein. A preferred non-human mammal is a dog. In certain embodiments, the dog is at least 9 months of age, or at least 12 months of age.

In certain embodiments, the present disclosure provides a method of treating dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions], comprising administering to a non-human mammal in need thereof an effective amount of a composition as disclosed herein comprising 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof. The composition may comprise particles of said compound having a particle size distribution of d50 of 15-30 μm, a d90 of 50-80 μm, a dv90 of ≤80 μm, and a dv50 of ≤30 μm. The composition may have an AV as described herein. A preferred non-human mammal is a dog. In certain embodiments, the dog is at least 9 months of age, or at least 12 months of age.

An effective amount of a compound of the invention can range from, for example, 0.25 mg to 100 mg. Specific amounts can be determined by the skilled person. Although these dosages are based on a patient having a mass of about 0.5 kg to about 80 kg, the diagnostician will be able to determine the appropriate dose for a subject whose mass falls outside of this weight range. An effective amount can range from, for example, 0.2 mg to 1.2 mg/kg of the patient, 0.4 mg to 1.0 mg/kg of the patient, 0.6 mg to 0.9 mg/kg of the patient, 0.8 mg/kg of the patient. The dosing regimen can be, for example, daily, twice daily, weekly, or monthly administration.

8. EXAMPLES

The following examples are provided to illustrate the invention and are not intended to be limiting in any way.

Example 1

2-[1-Cyclopropylsulfonyl-3-[4-(4,4,5,5-tetramethyl-1,3,2-dioxaborolan-2-yl)pyrazol-1-yl]azetidin-3-yl]acetonitrile 2-(1-Cyclopropylsulfonylazetidin-3-ylidene)acetonitrile (850 g) and 4-(4,4,5,5-tetramethyl-1,3,2-dioxaborolan-2-yl)-1H-pyrazole (874 g) were combined in acetonitrile (2.6 L). 1,8-Diazabicyclo[5.4.0]undec-7-ene (65 g) was added and the mixture was heated to 70° C. After 2.5 hours, the reaction mixture was cooled to ambient temperature over about 2 hours. Water (5.2 L) was added slowly to the mixture over about an hour and the mixture was stirred over about 3 hours. The solid that formed was collected by filtration and dried in vacuum at 45° C. for about 24 hours to give 2-[1-cyclopropylsulfonyl-3-[4-(4,4,5,5-tetramethyl-1,3,2-dioxaborolan-2-yl)pyrazol-1-yl]azetidin-3-yl]acetonitrile.

Example 2

2-(3-(4-(7H-pyrrolo[2,3-d]pyrimidin-4-yl)-1H-pyrazol-1-yl)-1-(cyclopropylsulfonyl)azetidin-3-yl)acetonitrile Potassium phosphate (829 g) was combined with water (1 L) and cooled to ambient temperature. THE (2 L) was added. 4-Chloropyrrolo[2,3-d]pyrimidine (200 g) was added followed by addition of di-tert-butyl dicarbonate (344 g). The reaction mixture was stirred at ambient temperature for 24 hours. The reaction mixture was sparged with nitrogen gas for 60 minutes. 2-[1-Cyclopropylsulfonyl-3-[4-(4,4,5,5-tetramethyl-1,3,2-dioxaborolan-2-yl)pyrazol-1-yl]azetidin-3-yl]acetonitrile (562 g) and Pd-134 (6.6 g) were added and the reaction temperature was raised to 60° C. After about 2 hours the aqueous layer was separated and silica thiol (40 g) was added and the reaction was stirred at 60° C. for 18 hours. The reaction mixture was filtered at 60° C. and then the filtrate cooled to 10-20° C. with stirring to give a solid which was collected by filtration and rinsed with cold THE before drying at 40-50° C. under vacuum for 2 hours to give tert-butyl 4-[1-[3-(cyanomethyl)-1-cyclopropylsulfonyl-azetidin-3-yl]pyrazol-4-yl]pyrrolo[2,3-d]pyrimidine-7-carboxylate (540 g).

tert-Butyl 4-[1-[3-(cyanomethyl)-1-cyclopropylsulfonyl-azetidin-3-yl]pyrazol-4-yl]pyrrolo[2,3-d]pyrimidine-7-carboxylate obtained above (540 g) was combined with n-butanol (3 L) and water (770 mL) and heated to 90° C. After 6 hours the reaction was cooled to 80° C. within 30 minutes and then stirred at 80° C. for 30 minutes before being cooled to 20° C. over 6 hours and stirred at 10-20° C. for 16 hours to give a solid which was filtered to give the title compound (as a wet cake) 460 g.

Example 3

2-(3-(4-(7H-pyrrolo[2,3-d]pyrimidin-4-yl)-1H-pyrazol-1-yl)-1-(cyclopropylsulfonyl)azetidin-3-yl)acetonitrile Potassium phosphate (829 g) was combined with water (1 L) and cooled to ambient temperature. THE (2 L) was added. 4-Chloropyrrolo[2,3-d]pyrimidine (200 g) was added followed by addition of di-tert-butyl dicarbonate (344 g). The reaction mixture was stirred at ambient temperature for 24 hours. The reaction mixture was sparged with nitrogen gas for 60 minutes. 2-[1-Cyclopropylsulfonyl-3-[4-(4,4,5,5-tetramethyl-1,3,2-dioxaborolan-2-yl)pyrazol-1-yl]azetidin-3-yl]acetonitrile (562 g) and Pd-134 (6.6 g) were added and the reaction temperature was raised to 60° C. After about 2 hours the aqueous layer was separated and silica thiol (40 g) was added and the reaction was stirred at 60° C. for 18 hours. The reaction mixture was filtered at 60° C. and then the filtrate cooled to 10-20° C. with stirring to give a solid which was collected by filtration and rinsed with cold THE before drying at 40-50° C. under vacuum for 2 hours to give tert-butyl 4-[1-[3-(cyanomethyl)-1-cyclopropylsulfonyl-azetidin-3-yl]pyrazol-4-yl]pyrrolo[2,3-d]pyrimidine-7-carboxylate (525 g).

tert-Butyl 4-[1-[3-(cyanomethyl)-1-cyclopropylsulfonyl-azetidin-3-yl]pyrazol-4-yl]pyrrolo[2,3-d]pyrimidine-7-carboxylate obtained above (540 g) was combined with n-butanol (3 L) and water (770 mL) and heated to 90° C. After 6 hours the reaction was cooled to 80° C. within 30 minutes and then stirred at 80° C. for 30 minutes before being cooled to 20° C. over 6 hours and stirred at 10-20° C. for 16 hours to give a solid which was filtered to give the title compound (as a wet cake) 454 g.

Example 4

2-(3-(4-(7H-pyrrolo[2,3-d]pyrimidin-4-yl)-1H-pyrazol-1-yl)-1-(cyclopropylsulfonyl)azetidin-3-yl)acetonitrile form II The wet cakes from Examples 2 and 3 (about 907 g) were combined in acetonitrile (4 L) and stirred at 60° C. for 2 hours. The reaction mixture was cooled to 20° C. over 6 hours and then stirred at 20° C. for 12 hours. The solid was collected by filtration, rinsed with acetonitrile, and dried under vacuum at 50-60° C. for 24 hours to give the title compound (695 g).

Example 5

2-(3-(4-(7H-pyrrolo[2,3-d]pyrimidin-4-yl)-1H-pyrazol-1-yl)-1-(cyclopropylsulfonyl)azetidin-3-yl)acetonitrile form I 2-(3-(4-(7H-pyrrolo[2,3-d]pyrimidin-4-yl)-1H-pyrazol-1-yl)-1-(cyclopropylsulfonyl)azetidin-3-yl)acetonitrile (104.1 mg) was combined with acetone (8 mL) and heated to 55° C. After 30 minutes, the reaction mixture was cooled at a rate of 0.02° C./minute to a temperature of 30° C. and then at a rate of 0.1° C./minute to a temperature of 5° C. while simultaneously adding heptane (12 mL) at a rate of 2.94 mL/hour to give a solid which was collected by filtration and dried to give the title compound (79.5 mg).

Example 6

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (152.4 mg) was combined with acetonitrile (8.1 mL) and heated to 80° C. After 30 minutes, the reaction mixture was cooled at a rate of 0.05° C./minute to a temperature of 5° C. to give a solid which was collected by filtration and dried to give the title compound (93.4 mg).

Example 7

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (157.8 mg) was combined with acetonitrile/water 96:4 (v/v) (4.2 mL) and heated to 80° C. After 30 minutes, the reaction mixture was cooled at a rate of 0.05° C./minute to a temperature of 5° C. to give a solid which was collected by filtration and dried to give the title compound (89.4 mg).

Example 8

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (5 g) was combined with acetonitrile/water 96:4 (v/v) (100 mL) and heated to 80° C. After about 75 minutes, the reaction mixture was cooled at a rate of 0.20° C./minute to a temperature of 70° C. and then seeds (2 portions of 0.25 g) were added and the cooling was continued at a rate of 0.05° C./minute to a temperature of 8° C. to give a solid. After about 6 hours the solid was collected by filtration and dried to give the title compound (4.88 g).

Example 9

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (20.6 mg) is combined with 4:1 (v/v) methanol/water (0.3 mL) having a water activity of about 0.5 and stir at 25° C. for 4 days, add additional with 4:1 (v/v) methanol/water (0.5 mL) and continue stirring at 25° C. for 6 days and then collect the solid by filter centrifugation (3 minutes, 5000 rpm, 0.2 μm PVDF membrane) to give the title compound.

Example 10

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (10 g) was combined with acetonitrile/water 96:4 (v/v) (250 mL) and heated to 72° C. After about 60 minutes, the reaction mixture was cooled at a rate of 0.20° C./minute to a temperature of 65° C. and then seeds (0.10 g) were added and the cooling was continued at a rate of 0.035° C./minute to a temperature of 35° C. to give a solid and then at a rate of 0.125° C./minute to a temperature of 5° C. to give a solid. After about 3 hours the solid was collected by filtration and dried to give the title compound (8.51 g).

Example 11

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (70.3 mg) was combined with 0.2 mL of 9:1 (v/v) acetone/water and heated to 60° C. while stirring. Additional 9:1 (v/v) acetone/water was slowly added a total of about 1.6 mL. The temperature was held at 60° C. for 1.5 hours and then the mixture was cooled at a rate of 0.05° C./minute to 10° C. and held at 10° C. for 2 hours and 45 minutes to give a solid. The solid was collected by filter centrifugation (2 minutes, 5000 rpm) to give the title compound.

Example 172

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (149.8 mg) was combined with acetonitrile (8.0 mL) and heated to 80° C. After 30 minutes, the reaction mixture was cooled at a rate of 0.02° C./minute to a temperature of 55° C. The reaction mixture was then cooled at a rate of 0.1° C./minute over the range 55° C. to 5° C. while simultaneously adding a total of 12 mL of isopropyl acetate at a rate of 1.44 mL/hour over the same duration as the cooling ramp from 55° C. to 5° C. to give a solid which was collected by filtration and dried to give the title compound (94.2 mg).

Example 13

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (208.5 mg) was combined with 0.2 mL of 3:1 (v/v) methanol/water and heated to 60° C. while stirring. Additional 3:1 (v/v) methanol/water was slowly added a total of about 23.2 mL. The temperature was held at 60° C. for 30 minutes and then the mixture was cooled at a rate of 0.05° C./minute to 10° C. and held at 10° C. for 20 minutes to give a solid. The solid was collected by filtration to give the title compound.

Example 14

2-(3-(4-(7H-pyrrolo[2,3-d]pyrimidin-4-yl)-1H-pyrazol-1-yl)-1-(cyclopropylsulfonyl)azetidin-3-yl)acetonitrile form III 2-(3-(4-(7H-pyrrolo[2,3-d]pyrimidin-4-yl)-1H-pyrazol-1-yl)-1-(cyclopropylsulfonyl)azetidin-3-yl)acetonitrile (60 mg) is combined with 2 mL of 5:1 (v/v) 1-butanol/water having a water activity of about 0.9 and stir at room temperature for 10 days and then collect the solid by filter centrifugation (2 minutes, 5000 rpm, 0.2 μm PTFE membrane) to give the title compound.

Example 15

2-(3-(4-(7H-pyrrolo[2,3-d]pyrimidin-4-yl)-1H-pyrazol-1-yl)-1-(cyclopropylsulfonyl)azetidin-3-yl)acetonitrile form III 2-(3-(4-(7H-pyrrolo[2,3-d]pyrimidin-4-yl)-1H-pyrazol-1-yl)-1-(cyclopropylsulfonyl)azetidin-3-yl)acetonitrile (33 mg) is combined with 0.4 mL of 3:2 (v/v) methanol/water having a water activity of about 0.7 and stir at about 20° C. for 14 days and then collect the solid by filter centrifugation (2 minutes, 4400 rpm, 0.2 μm PTFE membrane) to give the title compound.

Example 16

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.4 mg) is combined with acetophenone (1 mL) and stir at room temperature for 10 days and then collect the solid by filter centrifugation (2 minutes, 5000 rpm, 0.2 μm PTFE membrane) to give the title compound.

Example 17

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (59.9 mg) is combined with butyronitrile (2 mL) and stir at room temperature for 10 days and then collect the solid by filter centrifugation (2 minutes, 5000 rpm, 0.2 μm PTFE membrane) to give the title compound.

Example 18

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.3 mg) is combined with cyclohexanone (1.5 mL) and stir at room temperature for 10 days and then collect the solid by filter centrifugation (2 minutes, 5000 rpm, 0.2 μm PTFE membrane) to give the title compound.

Example 19

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.9 mg) is combined with dioxane (2 mL) and stir at room temperature for 10 days and then collect the solid by filter centrifugation (2 minutes, 5000 rpm, 0.2 μm PTFE membrane) to give the title compound.

Example 20

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.0 mg) is combined with ethyl formate (1.5 mL) and stir at room temperature for 10 days and then collect the solid by filter centrifugation (2 minutes, 5000 rpm, 0.2 μm PTFE membrane) to give the title compound.

Example 21

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (59.4 mg) is combined with methyl acetate (1.5 mL) and stir at room temperature for 10 days and then collect the solid by filter centrifugation (2 minutes, 5000 rpm, 0.2 μm PTFE membrane) to give the title compound.

Example 22

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.5 mg) is combined with nitrobenzene (2 mL) and stir at room temperature for 10 days and then collect the solid by filter centrifugation (2 minutes, 5000 rpm, 0.2 μm PTFE membrane) to give the title compound.

Example 23

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.5 mg) is combined with anisole (0.6 mL) and stir at 40° C. for 6 days and then collect the solid by filter centrifugation (2 minutes, 5000 rpm, 0.2 μm PTFE membrane) to give the title compound.

Example 24

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (59.8 mg) is combined with ethyl formate (0.6 mL) and stir at 40° C. for 6 days and then collect the solid by filter centrifugation (2 minutes, 5000 rpm, 0.22 μm PVDF membrane) to give the title compound.

Example 25

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.5 mg) is combined with isopropyl acetate (0.6 mL) and stir at 40° C. for 6 days and then collect the solid by filter centrifugation (2 minutes, 5000 rpm, 0.22 μm PVDF membrane) to give the title compound.

Example 26

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.4 mg) is combined with isopentanol (1 mL) and stir at 40° C. for 6 days and then collect the solid by filter centrifugation (2 minutes, 5000 rpm, 0.2 μm PTFE membrane) to give the title compound.

Example 27

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.4 mg) is combined with methyl isobutyl ketone (1 mL) and stir at 40° C. for 6 days and then collect the solid by filter centrifugation (2 minutes, 5000 rpm, 0.22 μm PTFE membrane) to give the title compound.

Example 28

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.6 mg) is combined with 3:1 (v/v) ethanol/water having a water activity of about 0.7 (0.9 mL) and stir at 40° C. for 6 days and then collect the solid by filter centrifugation (2 minutes, 5000 rpm, 0.22 μm PVDF membrane) to give the title compound.

Example 29

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (69.7 mg) is combined with 1-propanol (10.8 mL) and heated to 60° C. while stirring. Dimethylsulfoxide (2 mL) was slowly added to about an 85:15 (v/v) mixture of 1-propanol/DMSO. The temperature was held at 60° C. for about 1.5 hours and then the mixture was cooled at a rate of 0.05° C./minute to 10° C. and held at 10° C. for 7.5 hours then 1-propanol (5 mL) was added and then the mixture was stirred at 5° C. for 10 days to give a solid which was collected by filtration to give the title compound.

Example 30

2-(3-(4-(7H-pyrrolo[2,3-d]pyrimidin-4-yl)-1H-pyrazol-1-yl)-1-(cyclopropylsulfonyl)azetidin-3-yl)acetonitrile form III 2-(3-(4-(7H-pyrrolo[2,3-d]pyrimidin-4-yl)-1H-pyrazol-1-yl)-1-(cyclopropylsulfonyl)azetidin-3-yl)acetonitrile (70.6 mg) is combined with ethyl acetate saturated with water (0.2 mL) and heated to 60° C. while stirring and then added ethyl acetate (7.2 mL) and stirred at 60° C. for about 1.5 hours and then the mixture was cooled at a rate of 0.05° C./minute to 10° C. and then collect the solid by filter centrifugation (2 minutes, 5000 rpm, 0.2 μm PTFE membrane) to give the title compound.

Example 31

2-(3-(4-(7H-pyrrolo[2,3-d]pyrimidin-4-yl)-1H-pyrazol-1-yl)-1-(cyclopropylsulfonyl)azetidin-3-yl)acetonitrile form III 2-(3-(4-(7H-pyrrolo[2,3-d]pyrimidin-4-yl)-1H-pyrazol-1-yl)-1-(cyclopropylsulfonyl)azetidin-3-yl)acetonitrile (199.6 mg) is combined with ethyl acetate saturated with water (2.0 mL) and stirred at room temperature for 2 days and then collect the solid by filter centrifugation (2 minutes, 5000 rpm, 0.2 μm PTFE membrane) to give the title compound.

Example 32

2-(3-(4-(7H-pyrrolo[2,3-d]pyrimidin-4-yl)-1H-pyrazol-1-yl)-1-(cyclopropylsulfonyl)azetidin-3-yl)acetonitrile form I 2-(3-(4-(7H-pyrrolo[2,3-d]pyrimidin-4-yl)-1H-pyrazol-1-yl)-1-(cyclopropylsulfonyl)azetidin-3-yl)acetonitrile form III obtained from the material of Example 31 by drying under vacuum at 60° C. for about 69 hours to give the title compound.

Example 33

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.3 mg) is combined with ethanol (1 mL) and stir at 5° C. for 7 days and then collect the solid by filter centrifugation (2 minutes, 5000 rpm, 0.45 μm PVDF membrane) to give the title compound.

Example 34

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.4 mg) is combined with methanol (1 mL) and stir at 5° C. for 7 days and then collect the solid by filter centrifugation (2 minutes, 5000 rpm, 0.45 μm PVDF membrane) to give the title compound.

Example 35

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.0 mg) is combined with isopropanol (1 mL) and stir at 5° C. for 7 days and then collect the solid by filter centrifugation (2 minutes, 5000 rpm, 0.45 μm PVDF membrane) to give the title compound.

Example 36

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.3 mg) is combined with 1-butanol (2 mL) and stir at 5° C. for 7 days and then collect the solid by filter centrifugation (2 minutes, 5000 rpm, 0.45 μm PVDF membrane) to give the title compound.

Example 37

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (59.6 mg) is combined with ethanol (1 mL) and stir at 60° C. for 5 days and then collect the solid by filter centrifugation (2 minutes, 5000 rpm, 0.45 μm PVDF membrane) to give the title compound.

Example 38

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (59.9 mg) is combined with methanol (1 mL) and stir at 60° C. for 5 days and then collect the solid by filter centrifugation (2 minutes, 5000 rpm, 0.45 μm PVDF membrane) to give the title compound.

Example 39

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.1 mg) is combined with isopropanol (1.5 mL) and stir at 60° C. for 5 days and then collect the solid by filter centrifugation (2 minutes, 5000 rpm, 0.45 μm PVDF membrane) to give the title compound.

Example 40

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.6 mg) is combined with 1-butanol (1.5 mL) and stir at 60° C. for 5 days and then collect the solid by filter centrifugation (2 minutes, 5000 rpm, 0.45 μm PVDF membrane) to give the title compound.

Example 41

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (10.4 mg) is combined with acetonitrile (0.5 mL) and stir at 20° C. for 1 days and then collect the solid by filter centrifugation (1 minutes, 4500 g rcf, 0.2 μm PTFE membrane) to give the title compound.

Example 42

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (10.3 mg) is combined with acetone (0.5 mL) and stir at 20° C. for 1 days and then collect the solid by filter centrifugation (2 minutes, 4000 g rcf, 0.2 μm PTFE membrane) to give the title compound.

Example 43

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (20.6 mg) is combined with 4:1 (v/v) methanol/water having a water activity of about 0.5 (0.4 mL) and stir at 25° C. for 4 days, then added additional 4:1 (v/v) methanol/water (0.5 mL) and stir at 25° C. for 6 days and then collect the solid by filter centrifugation (3 minutes, 5000 rpm, 0.2 μm PVDF membrane) to give the title compound.

Example 44

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (539.9 mg) is combined with 1:1 (v/v) ethanol/acetone (18 mL) and stir at 60° C. for 45 minutes and then cooled at a rate of 0.05° C./minute to a temperature of 5° C. to give a solid which was collected by filtration and dried under vacuum at 40° C. to give the title compound.

Example 45

2-(3-(4-(7H-pyrrolo[2,3-d]pyrimidin-4-yl)-1H-pyrazol-1-yl)-1-(cyclopropylsulfonyl)azetidin-3-yl)acetonitrile form II 2-(3-(4-(7H-pyrrolo[2,3-d]pyrimidin-4-yl)-1H-pyrazol-1-yl)-1-(cyclopropylsulfonyl)azetidin-3-yl)acetonitrile (256.1 mg) is combined with 7:3 (v/v) acetone/isopropyl acetate (13.5 mL) and stir at 60° C. for 1 hour and then cooled at a rate of 0.02° C./minute to a temperature of 5° C. to give a solid which was collected by filtration and dried under vacuum at 40° C. to give the title compound.

Example 46

2-(3-(4-(7H-pyrrolo[2,3-d]pyrimidin-4-yl)-1H-pyrazol-1-yl)-1-(cyclopropylsulfonyl)azetidin-3-yl)acetonitrile form III 2-(3-(4-(7H-pyrrolo[2,3-d]pyrimidin-4-yl)-1H-pyrazol-1-yl)-1-(cyclopropylsulfonyl)azetidin-3-yl)acetonitrile (60 mg) is combined with 5:1 (v/v) 1-butanol/water having a water activity of about 0.9 (2 mL) and stir at room temperature for 10 days and then collect the solid by filter centrifugation (2 minutes, 5000 rpm, 0.2 μm PTFE membrane) to give the title compound.

Example 47

2-(3-(4-(7H-pyrrolo[2,3-d]pyrimidin-4-yl)-1H-pyrazol-1-yl)-1-(cyclopropylsulfonyl)azetidin-3-yl)acetonitrile form III 2-(3-(4-(7H-pyrrolo[2,3-d]pyrimidin-4-yl)-1H-pyrazol-1-yl)-1-(cyclopropylsulfonyl)azetidin-3-yl)acetonitrile (60.1 mg) is combined with 1:1 (v/v) acetonitrile/water having a water activity of about 0.9 (0.9 mL) and stir at 40° C. for 6 days and then collect the solid by filter centrifugation (2 minutes, 5000 rpm, 0.2 μm PTFE membrane) to give the title compound.

Example 48

2-(3-(4-(7H-pyrrolo[2,3-d]pyrimidin-4-yl)-1H-pyrazol-1-yl)-1-(cyclopropylsulfonyl)azetidin-3-yl)acetonitrile

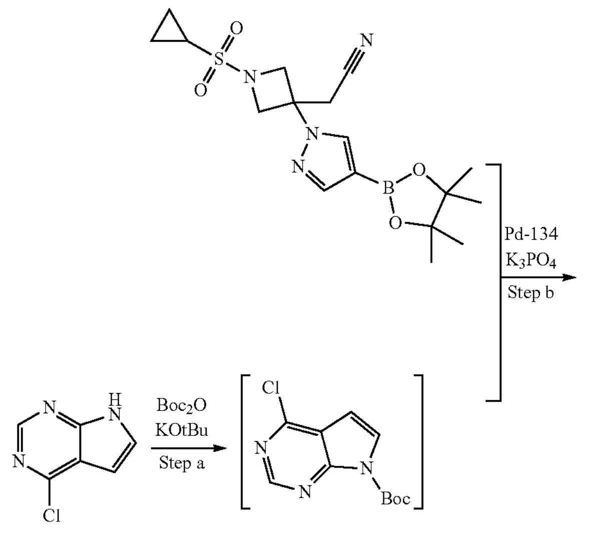

-continued

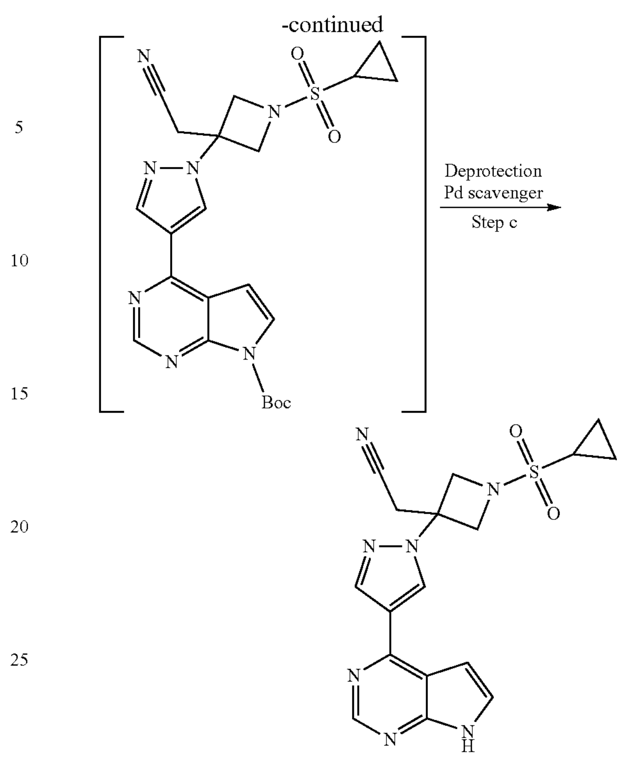

4-Chloropyrrolo[2,3-d]pyrimidine (100 g) and THE (890 g) were charged into reactor 2. The mixture was stirred at 20-30° C. until all the solid were dissolved. A pre-melted $Boc_2O$ (248.7 g) and THF (534 g) were charged into reactor 1. Subsequently KOtBu (11.0 g) was charged into reactor 1 slowly at 17-27° C. and rinsed with THF (89 g). The mixture in reactor 1 was stirred for 10-20 min at 17-27° C. The solution in reactor 2 was transferred into reactor 1 over 1-2 h at 17-27° C. Reactor 2 was rinsed with THE (89 g) and the washing solution was transferred into reactor 1. The mixture in reactor 1 was stirred for 1-3 h at 17-27° C. until reaction reached completion. After degassing with $N_2$ for 30-60 min, $H_2O$ (500 g) and $K_3PO_4·3H_2O$ (433.5 g) were charged into reactor 1 at 17-27° C. The reaction mixture was degassed with $N_2$ for 1-3 h. 2-[1-Cyclopropylsulfonyl-3-[4-(4,4,5,5-tetramethyl-1,3,2-dioxaborolan-2-yl)pyrazol-1-yl]azetidin-3-yl]acetonitrile (263.1 g) and $PdCl_2$—Xtranphos (2.46 g) was charged into reactor 1 under $N_2$ protection. The resulting mixture was exchanged with $N_2$ three times and then stirred at 50-60° C. for 1-3 h until reaction reached completion. After standing at 50-60° C. for 20-40 min, the aqueous phase was separated and discarded. The reaction mixture was washed with 10% KCl solution (640 g) once, then water (500 g) two times. The organic layer was concentrated to 12-13 V by atmospheric distillation≤75° C. Acetonitrile (1943 g) was added into reactor 1 and the organic layer was concentrated to 20-30 V by atmospheric distillation≤85° C. Acetonitrile (1476 g) was added into reactor 1 and the organic layer was concentrated to 20-30 V by atmospheric distillation≤85° C. Checked residual THF to confirm it reached acceptance level of ≤1%. Water (300 g) and silica thiol (20.0 g) were added into reactor 1 and the reaction was heated to 70-80° C. The mixture was stirred at 70-80° C. for 18-24 h until reaction reached completion. The reaction mixture was cooled to 60-70° C. and filtered through a bed of diatomite (20 g) into reactor 3. Reactor 1 was rinsed with acetonitrile (540 g) and the washing solution was filtered into reactor 3. The mixture in reactor 3 was concentrated to 31-33 V by atmospheric distillation at 70-85° C. Acetonitrile (1554 g) was added into reactor 3 by continuous atmospheric distillation at 70-85° C. Seeds (0.5 g) were charged and stirred at 75-85° C. for 30-60 min. Optional acetonitrile (389 g) was charged into reactor 3 by continuous atmospheric distillation at 70-85° C. to ensure KF≤4.0%. The reaction mixture was cooled to 15-25° C. over 5-7 h and aged for additional 2-4 h to give a solid which was filtered, and washed with acetonitrile (311 g). The wet cake was dried at 45-55° C. under vacuum for 20-24 h to give the title compound (227 g). Note: The quantities of materials used in Example 48 is a nominal amount of a batch with 9.0 kg of 4-chloropyrrolo[2,3-d]pyrimidine as the input limiting reagent.

Example 49

Control of pruritus and skin lesions associated with allergic dermatitis in dogs.

This study evaluated 2-(3-(4-(7H-pyrrolo[2,3-d]pyrimidin-4-yl)-1H-pyrazol-1-yl)-1-(cyclopropylsulfonyl)azetidin-3-yl)acetonitrile for control of pruritus and skin lesions associated with allergic dermatitis in dogs.

Oral tablets were prepared containing Form II 2-(3-(4-(7H-pyrrolo[2,3-d]pyrimidin-4-yl)-1H-pyrazol-1-yl)-1-(cyclopropylsulfonyl)azetidin-3-yl)acetonitrile, as follows. Oral tablet blends were prepared containing crystal Form II 2-(3-(4-(7H-pyrrolo[2,3-d]pyrimidin-4-yl)-1H-pyrazol-1-yl)-1-(cyclopropylsulfonyl)azetidin-3-yl)acetonitrile, microcrystalline cellulose, pregelatinized starch, dicalcium phosphate dehydrate, oxide pigment, and magnesium stearate. The tablet blends were pressed giving tablet cores containing 2.4 mg, 3.6 mg, 5.4 mg, and 16 mg of crystal Form II 2-(3-(4-(7H-pyrrolo[2,3-d]pyrimidin-4-yl)-1H-pyrazol-1-yl)-1-(cyclopropylsulfonyl)azetidin-3-yl)acetonitrile, as well as a placebo core. The tablet cores were coated with a mixture containing water and Opadry 20A150011 Red, thereby giving the final oral tablets for the study.

TABLE 1

Tablet Blends

| Ingredient | Quantity (% w/w) | Placebo Quantity (% w/w) |
|---|---|---|
| 2-(3-(4-(7H-pyrrolo[2,3-d]pyrimidin-4-yl)-1H-pyrazol-1-yl)-1-(cyclopropylsulfonyl)azetidin-3-yl)acetonitrile | 2.4 | 0.0 |
| Microcrystalline cellulose (Vivapur 302) | 52.0 | 52.0 |
| Pregelatinized starch (Starch 1500) | 12.0 | 12.0 |
| Dicalcium phosphate dihydrate (Di Tab) | 32.4 | 34.8 |
| Oxide pigment PB-150021 RED | 0.2 | 0.2 |
| Magnesium Stearate (Hyqual) | 1.0 | 1.0 |

A four-arm, blinded, randomized, placebo-controlled study was conducted to assess the efficacy of daily administration of 2-(3-(4-(7H-pyrrolo[2,3-d]pyrimidin-4-yl)-1H-pyrazol-1-yl)-1-(cyclopropylsulfonyl)azetidin-3-yl)acetonitrile for control of pruritus and skin lesions associated with allergic dermatitis in dogs. Subjects were randomized to one of the following treatment arms: API-containing Tablets, 0.25-0.40 mg/kg Body Weight; API-containing Tablets, 0.40-0.60 mg/kg Body Weight; API-containing Tablets, 0.60-0.80 mg/kg Body Weight; and Placebo Tablets, 0.0 mg/kg Body Weight.

Dogs enrolled in the study received once daily treatment for approximately 28 days. Baseline data (clinical history, concomitant therapies, body weight, physical examinations and assessments of pruritus and atopic dermatitis) were collected for each dog at enrollment (Day 0). Additional health assessments, physical examinations, body weight measurements, assessments of pruritus and atopic dermatitis, and collection of blood samples for hematology, serum chemistry and pharmacokinetic (PK) analysis occurred consistent with standard testing protocols.

The primary effectiveness variable was treatment success. A treatment success was defined as a 2 unit or more reduction from baseline on the 10-unit owner-assessed pruritus Visual-Analog Scale (VAS) in at least 70% of the first 7 treatment days (i.e., in at least 5 of the first 7 treatment days). Dogs withdrawn from the study within the first 7 days of treatment due to a perceived lack of effectiveness were considered treatment failures. The minimum effective dose was defined in the protocol as the dose at which treatment success is achieved in at least 50% of the dogs.

Table 2 shows that the highest dose of 2-(3-(4-(7H-pyrrolo[2,3-d]pyrimidin-4-yl)-1H-pyrazol-1-yl)-1-(cyclopropylsulfonyl)azetidin-3-yl)acetonitrile (0.60-0.80 mg/kg) had a response rate of 0.7188 (95% confidence interval 0.5331, 0.8512) which is statistically significantly higher than the placebo response rate of 0.2935 (0.1571, 0.4808); p-value for the comparison (on the logit scale) is 0.0006. Thus, the highest dose group (0.6-0.8 mg/kg) achieved the primary endpoint for treatment success. Furthermore, once daily dosing with 0.6-0.8 mg/kg showed significant improvements in pruritus from first dose, and the group showed a significant improvement in lesion scores at day 28 in the study. The estimated marginal mean response rate for low (0.24-0.4 mg/kg) and medium dose (0.4-0.6 mg/kg) were also higher than the placebo rate. This result is based on a generalized linear mixed model with fixed effect terms for treatment and Day 0 VAS score. Random effects were fit for site and site treatment with a variance component covariance structure and a compound symmetry covariance structure was fit for individual dogs.

TABLE 2

Treatment Success Generalized Linear Mixed Model Summary

| Treatment group | Number of dogs | LSMean | Std Err | 95% Confidence Limits | p-value vs placebo |
|---|---|---|---|---|---|
| 0.25-0.40 mg/kg | 43 | 0.4640 | 0.0919 | (0.2900, 0.6472) | 0.1336 |
| 0.40-0.60 mg/kg | 42 | 0.5590 | 0.0891 | (0.3772, 0.7261) | 0.0227 |
| 0.60-0.80 mg/kg | 42 | 0.7188 | 0.0809 | (0.5331, 0.8512) | 0.0006 |
| Placebo 0.0 mg/kg | 42 | 0.2935 | 0.0824 | (0.1571, 0.4808) | |

Example 50

Micronization was begun with a short "setup" run of approximately 300 grams was performed using a feed rate of 9.6 kg/hr. Venturi/mill pressures were 10 psi. The sample pulled from this run (sample "I") had a dv10 value of 4, a dv50 value of 20, and a dv90 value of 53.

Example 51

Particle size distribution method of 2-(3-(4-(7H-pyrrolo[2,3-d]pyrimidin-4-yl)-1H-pyrazol-1-yl)-1-(cyclopropylsulfonyl)azetidin-3-yl)acetonitrile.

Method: 150 to 175 mg 2-(3-(4-(7H-pyrrolo[2,3-d]pyrimidin-4-yl)-1H-pyrazol-1-yl)-1-(cyclopropylsulfonyl)azetidin-3-yl)acetonitrile sample are dispersed with 1 ml Tween20/water mixture (10/90 v/v %) to a paste in a beaker. The entire paste is then transferred to the measuring cuvette (beaker is rinsed out with water for complete sample transfer) and dispersed in 300 ml water. To homogenize the suspension in the measuring cuvette, the pump speed is set to 600 rpm. Before measurement the sample is stirred for 30 seconds. The optical concentration should be in the range of approximately 15 to 20% but the value depends strongly on the particle size distribution in the sample. If the 15 to 20% range is not reached either more sample paste must be added or the sample has to be diluted with water.

Equipment: a Helos laser diffractometer from Sympatec is used. Suspensions are measured using a Quixel cell. Dry measurement is done using the Rodos unit. Evaluation is done using the Paqxos software. Using this PSD method to analyze the material produced and milled as in Example 50, the results were a dv10 value of 4, a dv50 value of 20, and a dv90 value of 51.

TABLE 3

Method Parameters for Example 51

| Parameter | Description |
|---|---|
| Cuvette temperature | 20° C. |
| Cuvette diameter | 2 mm |
| Cuvette filling level | low |
| Trigger condition (start) | Copt ≥ 1% |
| Trigger condition (valid) | Always |
| Trigger condition (stop) | 5 sec Copt ≤ 1% or 10 sec real time |
| Ultrasonication | No |
| Pump speed | 600 turns/min |
| Calculation mode | HRLD |
| Lens | R5 (if required lens changing according to the expected particle size distribution) |

What is claimed is:

1. A tablet comprising substantially polymorphically pure crystalline 2-(3-(4-(7H-pyrrolo[2,3-d]pyrimidin-4-yl)-1H-pyrazol-1-yl)-1-(cyclopropylsulfonyl) azetidin-3-yl)acetonitrile, wherein the tablet has an Acceptance Value of 5 or lower, wherein the polymorphically pure crystalline 2-(3-(4-(7H-pyrrolo[2,3-d]pyrimidin-4-yl)-1H-pyrazol-1-yl)-1-(cyclopropylsulfonyl) azetidin-3-yl)acetonitrile is in the form of particles having a particle size distribution characterized by d50 of 15-30 μm, a d90 of 50-80 μm, a dv90 of ≤80 μm, and a dv50 of ≤30 μm, and wherein the substantially polymorphically pure crystalline 2-(3-(4-(7H-pyrrolo[2,3-d]pyrimidin-4-yl)-1H-pyrazol-1-yl)-1-(cyclopropylsulfonyl) azetidin-3-yl) acetonitrile is characterized by the X-ray powder diffraction pattern comprising a peak at 5.34°, 10.68°, 14.26°, 16.06°, 16.39°, 16.48°, 18.26°, 18.65°, 21.05°, 21.76°, 22.68°, or 26.75° (±0.2° 2θ).

2. The tablet of claim 1, wherein the tablet has an Acceptance Value of 3.5 or lower.

3. The tablet of claim 1, wherein the tablet is coated.

4. The tablet of claim 1, wherein the tablet comprises from 1 mg to 20 mg of substantially polymorphically pure crystalline 2-(3-(4-(7H-pyrrolo[2,3-d]pyrimidin-4-yl)-1H-pyrazol-1-yl)-1-(cyclopropylsulfonyl) azetidin-3-yl)acetonitrile.

5. The tablet of claim 1, wherein the tablet comprises 4.8 mg, 6.4 mg, 8.5 mg, or 15 mg of substantially polymorphically pure crystalline 2-(3-(4-(7H-pyrrolo[2,3-d]pyrimidin-4-yl)-1H-pyrazol-1-yl)-1-(cyclopropylsulfonyl) azetidin-3-yl) acetonitrile.

6. A composition comprising particles of substantially polymorphically pure crystalline 2-(3-(4-(7H-pyrrolo[2,3-d]pyrimidin-4-yl)-1H-pyrazol-1-yl)-1-(cyclopropylsulfonyl) azetidin-3-yl)acetonitrile, wherein the particles have a particle size distribution characterized by d50 of 15-30 μm, a d90 of 50-80 μm, a dv90 of ≤80 μm, and a dv50 of ≤30 μm, wherein the substantially polymorphically pure crystalline 2-(3-(4-(7H-pyrrolo[2,3-d]pyrimidin-4-yl)-1H-pyrazol-1-yl)-1-(cyclopropylsulfonyl) azetidin-3-yl)acetonitrile is characterized by the X-ray powder diffraction pattern comprising a peak at 5.34°, 10.68°, 14.26°, 16.06°, 16.39°, 16.48° 18.26°, 18.65°, 21.05°, 21.76°, 22.68°, or 26.75° (±0.2° 2θ).

7. The composition of claim 6, wherein the composition further comprises microcrystalline cellulose, pregelatinized starch, calcium phosphate dibasic dihydrate, povidone, magnesium stearate, coating, or any combination thereof.

8. The composition of claim 6, wherein the composition is an oral dosage form.

9. The composition of claim 8, wherein the oral dosage form comprises from 1 mg to 20 mg of substantially polymorphically pure crystalline 2-(3-(4-(7H-pyrrolo[2,3-d]pyrimidin-4-yl)-1H-pyrazol-1-yl)-1-(cyclopropylsulfonyl) azetidin-3-yl)acetonitrile having a particle size distribution characterized by d50 of 15-30 μm, a d90 of 50-80 μm, a dv90 of ≤80 μm, and a dv50 of ≤30 μm.

10. The composition of claim 8, wherein the oral dosage form comprises 4.8 mg, 6.4 mg, 8.5 mg, or 15 mg of substantially polymorphically pure crystalline 2-(3-(4-(7H-pyrrolo[2,3-d]pyrimidin-4-yl)-1H-pyrazol-1-yl)-1-(cyclopropylsulfonyl) azetidin-3-yl)acetonitrile having a particle size distribution characterized by d50 of 15-30 μm, a d90 of 50-80 μm, a dv90 of ≤80 μm, and a dv50 of ≤30 μm.

11. A method of treating a dermatological condition comprising administering to a non-human mammal in need thereof an effective amount of a tablet according to claim 1.

12. The method of claim 11, wherein the dermatological condition is atopic dermatitis or pruritus.

13. The method of claim 11, wherein the non-human mammal is a dog.

14. A method of treating a dermatological condition comprising administering to a non-human mammal in need thereof an effective amount of the composition of claim 6.

15. The method of claim 14, wherein the dermatological condition is atopic dermatitis or pruritus.

16. The method of claim 14, wherein the non-human mammal is a dog.

* * * * *